(12) United States Patent
Kanikanti et al.

(10) Patent No.: US 9,744,127 B2
(45) Date of Patent: Aug. 29, 2017

(54) NON-STARCH BASED SOFT CHEWABLES

(75) Inventors: Venkata-Rangarao Kanikanti, Leverkusen (DE); Hans-Juergen Hamann, Dormagen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 13/878,901

(22) PCT Filed: Oct. 11, 2011

(86) PCT No.: PCT/EP2011/067699
§ 371 (c)(1),
(2), (4) Date: Apr. 11, 2013

(87) PCT Pub. No.: WO2012/049156
PCT Pub. Date: Apr. 19, 2012

(65) Prior Publication Data
US 2013/0197006 A1     Aug. 1, 2013

Related U.S. Application Data

(60) Provisional application No. 61/392,150, filed on Oct. 12, 2010.

(51) Int. Cl.
*A61K 9/00* (2006.01)
*A61K 9/20* (2006.01)

(52) U.S. Cl.
CPC .......... *A61K 9/0056* (2013.01); *A61K 9/2018* (2013.01); *A61K 9/2022* (2013.01); *A61K 9/2054* (2013.01); *A61K 9/2059* (2013.01)

(58) Field of Classification Search
None
See application file for complete search history.

(56) References Cited

U.S. PATENT DOCUMENTS

| | | | |
|---|---|---|---|
| 4,382,892 A | 5/1983 | Hayakawa et al. |
| 4,472,405 A | 9/1984 | Stern et al. |
| 4,670,444 A | 6/1987 | Grohe et al. |
| 4,704,459 A | 11/1987 | Todo et al. |
| 4,730,000 A | 3/1988 | Chu |

(Continued)

FOREIGN PATENT DOCUMENTS

| | | |
|---|---|---|
| GB | 2300103 A | 10/1996 |
| WO | 0200202 A1 | 1/2002 |

(Continued)

OTHER PUBLICATIONS

Bayer HealthCare LLC, "Freedom of Information Summary, NADA 141-007", (2006).*

*Primary Examiner* — Ernst V Arnold
*Assistant Examiner* — Kyung Sook Chang
(74) *Attorney, Agent, or Firm* — McBee Moore Woodward & Vanik IP, LLC; Chester Moore; Susan McBee

(57) ABSTRACT

The present invention generally relates to soft chewables, especially suitable for delivering active ingredients to animals and processes for the preparation thereof. In various embodiments, the soft chewable comprises a pharmaceutically effective amount of at least one active ingredient, a flavoring agent, a disintegrant, a humectant, an antioxidant, a preservative, and water. In accordance with preferred embodiments, the soft chewable is essentially free of starch, oil, glycols, waxes, and soy products.

13 Claims, 3 Drawing Sheets

(56) References Cited

U.S. PATENT DOCUMENTS

| | | | |
|---|---|---|---|
| 4,861,779 A | | 8/1989 | Jefson et al. |
| 5,244,669 A | * | 9/1993 | Satoh .................... A61K 9/5073 424/401 |
| 5,573,777 A | | 11/1996 | Serpelloni et al. |
| 6,159,932 A | | 12/2000 | Mencke et al. |
| 7,914,816 B2 | | 3/2011 | Kalbe et al. |
| 2004/0037869 A1 | * | 2/2004 | Cleverly et al. ............. 424/442 |
| 2004/0151759 A1 | * | 8/2004 | Cleverly ............. A61K 9/0056 424/442 |
| 2006/0222684 A1 | | 10/2006 | Isele |
| 2006/0233873 A1 | | 10/2006 | Meissonnier et al. |
| 2008/0160067 A1 | | 7/2008 | Boeckh et al. |
| 2009/0117181 A1 | * | 5/2009 | Uehara ................ A61K 9/2054 424/464 |

FOREIGN PATENT DOCUMENTS

| | | |
|---|---|---|
| WO | 2004014143 A1 | 2/2004 |
| WO | 2004016252 A1 | 2/2004 |
| WO | 2005013714 A1 | 2/2005 |
| WO | 2005018323 A1 | 3/2005 |
| WO | 2005062782 A2 | 7/2005 |
| WO | 2007067582 A2 | 6/2007 |
| WO | 2008030469 A2 | 3/2008 |
| WO | WO 2008134819 A1 * | 11/2008 |

* cited by examiner

NON-STARCH BASED SOFT CHEWABLES

FIELD OF THE INVENTION

The present invention generally relates to soft chewables, especially suitable for delivering active ingredients to animals and processes for the preparation thereof.

BACKGROUND OF THE INVENTION

Starch-based soft chewables are generally known in the art. Starch-based extrudates containing drug substances, specific aromas, and bodying agents are described in European Patent No. 1298655 B1 (Kalbe et al.) Kalbe et al. also describe processes for preparing the starch-based extrudates at a temperature less than 150° C. The examples of this patent describe soft chewables containing either 55% wheat flour or 45% maize starch as the primary matrix component. The extrusion temperature mentioned in the examples is 120° C. which is very high for practical purposes especially when the active ingredient is thermolabile.

Ductile soft chewables containing partially pre-gelatinized starch as the primary matrix material are reported in U.S. Patent Application Publication No. 2008/0222684 (Isele). Isele mentions that partially pre-gelatinized starch is needed for obtaining the desired ductility of the final product. Accordingly, examples 1-3 of Isele describe chewables containing 41%, 31.9%, and 36.7% pre-gelatinized starch, respectively. The chewables are prepared by an extrusion process that requires the equipment to be pre-cooled below room temperature (i.e., <10° C.). The mixture to be extruded is also cooled continuously during the extrusion process with the help of external coolers so that the product temperature does not exceed 40° C. The chewables are filled into boxes and cured for about 24 hours at ambient temperature and a relative humidity of less than 60%. Each formulation contains 1.5% sodium chloride to enhance payability and to bind moisture.

Soft chews for equines and canines are described in International Patent Publication WO 2004/014143 (Huron). The chewables essentially contain flavoring, starch, sugar, and an oil component. The moisture content is less than 15%. The equine soft chews mentioned in example 18 do not contain meat flavor. The disintegration time was reported as 14.45 min. However, the meat based canine chews reported in example 2 show a disintegration time of greater than 60 min. For both examples, melted polyethylene glycol (70° C.) was used to prepare a wet granulation mix.

Great Britain Patent No. 2300103B (Gilberston) describes palatable dog biscuits containing partially gelatinized starch and creatine prepared by an extrusion process at temperatures up to 130° C. This process is unsuitable for thermolabile drugs.

Conventional use of starch materials (e.g., corn starch, wheat starch, rice starch, pregelatinized starch and partially gelatinized starch) as binders, moisture retention aids and/or bodying agents to render the formulation soft and chewable can inhibit the desired disintegration of the soft chewable and dissolution profile of the active ingredient, in particular, the starch material swells when contacted with water and can prohibit rapid disintegration of the soft chewable product and subsequent dissolution of the active ingredient from the soft chew matrix in a reasonable amount of time. Other conventional ingredients used in soft chewable formulations may also have deleterious effects on the desired disintegration and dissolution profile of the product. For example, oils and waxes are often used as humectants to prevent drying and improve storage stability of the soft chewable. However, these hydrophobic ingredients can finely coat the active ingredient with a moisture-repelling barrier and thereby inhibit dissolution of the active ingredient upon administration.

Other materials used in conventional soft chewable formulations also have drawbacks. Soya products (e.g., hydrolyzed soy protein) are used as a moisture retention aid and/or filler or extender and also improve payability. However, soya products tend to exhibit a certain lack of uniformity and, as a result, when used as excipients contribute undesirably to interbatch variations and undermine quality control. Glycols (e.g., polyethylene glycol (PEG)) are another example of a humectant or moisture retention aid. Higher molecular weight glycols are typically added, to the formulation as a melt and the resulting soft chewable must be tempered for a sufficient period of time to allow the glycol to resolidify, which complicates and undesirably extends processing.

Therefore, while soft chewable formulations are known, there remains a need for an improved soft chewable for delivering drugs and other active ingredients to animals that is palatable, storage stable and disintegrates relatively quickly upon administration while avoiding some of the drawbacks associated with conventional soft chewable formulations and processing.

Further, there remains a need for processes for preparing improved soft chewables that may be practiced economically on a commercial scale at ambient or room temperatures and that are suitable for use with thermolabile drugs.

SUMMARY OF THE INVENTION

Briefly, therefore, the present invention is directed to soft chewables, especially suitable for delivering active ingredients to animals. In accordance with one embodiment, a soft chewable comprising (a) a pharmaceutical effective amount of at least one active ingredient, (b) a flavoring agent, (c) a disintegrant, (d) a humectant, (e) a binder, (f) an antioxidant, (g) a preservative; and (h) water is provided.

The present invention is further directed to processes for preparing the soft chewable. In one embodiment, the process comprises (a) preparing, at ambient temperature (about 20-25° C.), a mixture comprising at least one active ingredient, a flavoring agent, an antioxidant, a preservative, and a disintegrant; (b) preparing a granulation fluid comprising a humectant, water, and a binder; (c) combining under agitation the granulation fluid and the mixture to form a dough; (d) forming the soft chewable from the dough; and (e) reducing the moisture content of the soft chewable.

Other objects and features will be in part apparent and in part pointed out hereinafter.

DESCRIPTION OF THE PREFERRED EMBODIMENTS

Figure 1:
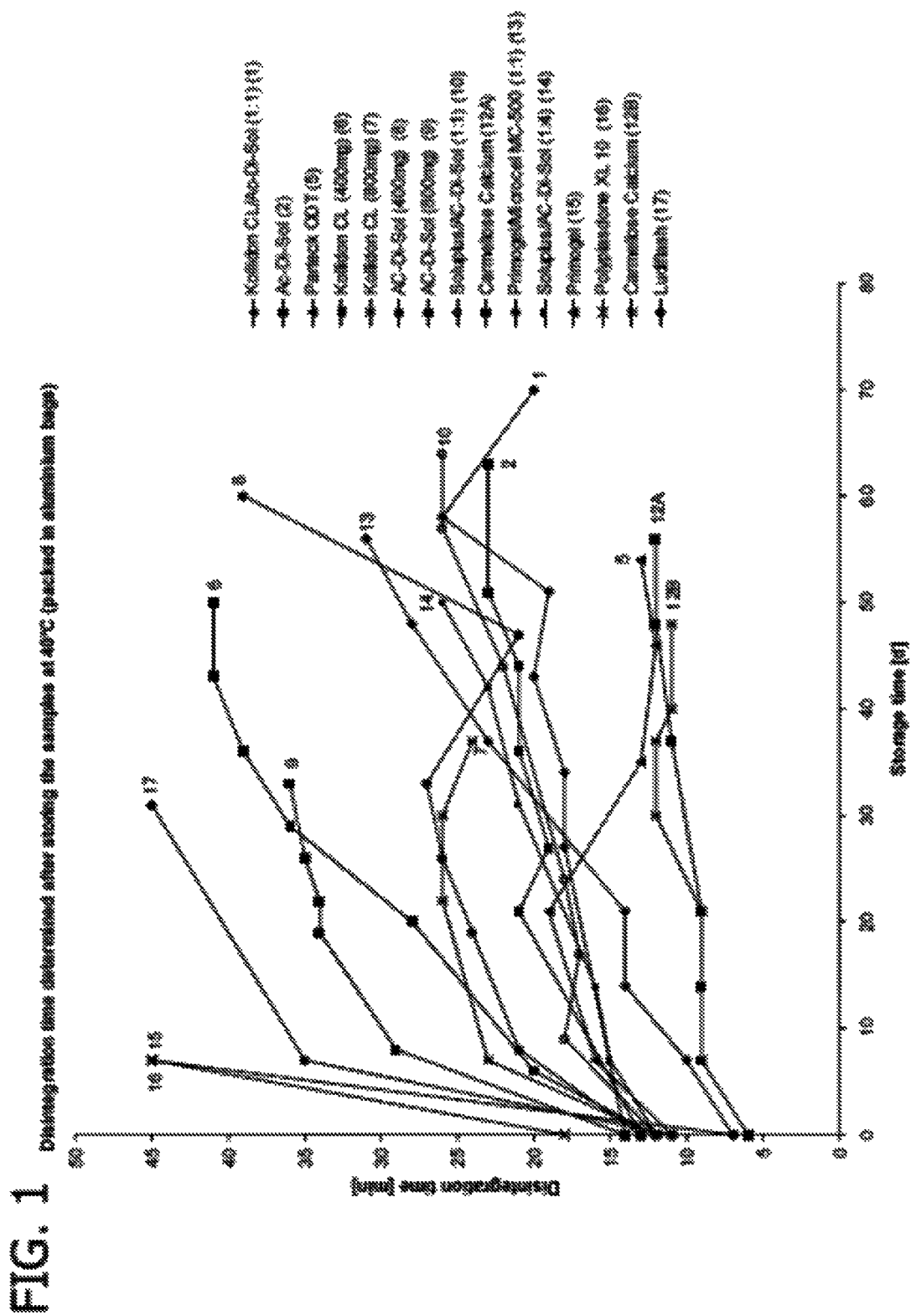
FIG. 1 shows a plot of the disintegration time for soft chewable treats containing various disintegrants as described in Example 1.

The present invention is directed to a soft, chewable product (i.e., a soft chewable), suitable for delivering one or more active ingredients to an animal.

The present invention is also directed to a process for preparing a soft chewable. As described in greater detail below, the process includes combining dry components of the formulation with a granulation fluid to form a moist homogeneous dough.

In accordance with the present invention, soft chewables have been devised that overcome some of the deficiencies of starch-based soft chews and other conventional formulations. The soft chewables of the present invention combine at least one active ingredient, a flavoring agent, a humectant, an antioxidant, a preservative, a binder and water along with a disintegrant component comprising one or more disintegrants or so-called super-disintegrants in an amount which exceeds the conventional concentrations at which such disintegrants are typically employed. In particular, applicants have discovered that by employing a disintegrant component comprising selected disintegrants and in a higher concentration, the disintegrant component can effectively provide a substantial portion of the soft chewable matrix which disintegrates rapidly upon administration. The soft chewables are palatable and advantageously retain their disintegration characteristics even after prolonged storage. In accordance with preferred embodiments, the soft chewables of the present invention are free or essentially free of ingredients that might undermine the desired disintegration of the soft chewable and/or dissolution profile of the active ingredient(s) such as starch materials, oils, and waxes. Furthermore, by proper selection of the other ingredients, the soft chewables disclosed herein are free or essentially free of soya products and glycols such as polyethylene glycol. As used herein, the phrase "essentially free" means an amount of the ingredient that is no more than that which would exhibit the undesirable properties of the ingredient in the soft chewable. Typically, this amount is less than about 2% by weight, more typically less than about 1% by weight.

The soft chewables of the present invention remain soft and pliable over extended periods of time and are readily adapted to manufacture by simplified and economical processes.

The present invention and its embodiments:
1. A soft chewable comprising:
   (a) a pharmaceutically effective amount of at least one active ingredient;
   (b) a flavoring agent;
   (c) a disintegrant;
   (d) a humectant;
   (e) a binder
   (f) an antioxidant;
   (g) optionally a preservative; and
   (h) water.
2. The soft chewable of item 1 comprising (g) a preservative.
3. The soft chewable of item 1 or 2 wherein the soft chewable disintegrates in less than about 25 minutes as determined in accordance with method 2.9.1 (Test B) of the European Pharmacopoeia 6.0.
4. The soft chewable of item 1 or 2 wherein the soft chewable disintegrates in less than about 20 minutes as determined in accordance with method 2.9.1 (Test B) of the European Pharmacopoeia 6.0.
5. The soft chewable of stem 1 or 2 wherein the soft chewable disintegrates in less than about 15 minutes as determined in accordance with method 2.9.1 (test B) of the European Pharmacopoeia 6.0.
6. The soft chewable of any of items 1 to 5 wherein the disintegrant constitutes at least about 10 wt %, at least about 12 wt %, at least about 15 wt %, at least about 17 wt %, at least about 20 wt %, at least about 25 wt %, at least about 30 wt %, at least about 40 wt %, or at least about 50 wt % of the soft chewable.
7 The soft chewable of any of items 1 to 6 wherein the disintegrant constitutes from about 10 wt % to about 60 wt %, from about 10 wt % to about 50 wt %, from about 10 wt % to about 40 wt %, from about 10 wt % to about 35 wt %, from about 10 wt % to about 30 wt %, from about 12 wt % to about 30 wt %, or from about 15 wt % to about 30 wt % of the soft chewable.
8. The soft chewable of any of items 1 to 7 wherein the disintegrant is selected from the group consisting of carmellose calcium, directly compressible mannitol, crosslinked povidone, croscarmellose sodium, a mixture of directly compressible mannitol and croscarmellose sodium, and combinations thereof.
9. The soft chewable of any of items 1 to 8 wherein the disintegrant is selected from the group consisting of a mixture of croscarmellose sodium and directly compressible mannitol, a mixture of croscarmellose sodium and polyvinyl caprolactam-polyvinyl acetate-polyethylene glycol graft copolymer, a mixture of croscarmellose sodium and crosslinked povidone, a mixture of sodium starch glycolate and microcrystalline cellulose, and combinations thereof.
10. The soft chewable of any of items 1 to 9 wherein the disintegrant comprises carmellose calcium.
11. The soft chewable of any of items 1 to 10 wherein the disintegrant comprises directly compressible mannitol
12. The soft chewable of any of items 1 to 11 wherein the disintegrant comprises a mixture of croscarmellose sodium and directly compressible mannitol.
13. The soft chewable of any of items 1 to 12 wherein the disintegrant comprises directly compressible mannitol having a mean particle size of about 200 µm.
14. The soft chewable of any of items 1 to 13 wherein the flavoring agent constitutes at least about 1 wt %, at least about 5 wt %, at least about 10 wt %, at least about 15 wt %, at least about 20 wt %, or at least about 25 wt % of the soft chewable.
15. The soft chewable of any of items 1 to 14 wherein the flavoring agent constitutes from about 1 wt % to about 40 wt %, from about 5 wt % to about 40 wt %, from about 10 wt % to about 35 wt %, or from about 15 wt % to about 30 wt % of the soft chewable.
18. The soft chewable of any of items 1 to 15 wherein the flavoring agent comprises an animal-derived product.
17. The soft chewable of any of items 1 to 18 wherein the humectant constitutes at least about 10 wt %, at least about 15 wt %, or at least about 20 wt % of the soft chewable.
18. The soft chewable of any of items 1 to 17 wherein the humectant constitutes from about 5 wt % to about 50 wt %, from about 10 wt % to about 45 wt %, from about 15 wt % to about 40 wt %, from about 20 wt % to about 35 wt %, from about 20 wt % to about 30 wt %, or about 25 wt % of the soft chewable.
19. The soft chewable of any of items 1 to 18 wherein the humectant comprises glycerin.
20. The soft chewable of any of items 1 to 19 wherein the antioxidant constitutes at least about 0.01 wt %, at least about 0.1 wt %, at least about 1 wt %, at least about 2 wt %, or at least about 5 wt % of the soft chewable.

21. The soft chewable of any of items 1 to 20 wherein the antioxidant constitutes from about 0.01 wt % to about 15 wt %, from 0.1 wt % to 15 wt %, from about 1 wt % to 10 wt %, 5 wt % to about 15 wt %, or from about 5 wt % to 10 wt % of the soft chewable.

22. The soft chewable of any of items 1 to 21 wherein the antioxidant comprises citric acid.

23. The soft chewable of any of items 1 to 22 wherein the antioxidant comprises propyl gallate.

24. The soft chewable of any of items 1 to 23 wherein the antioxidant comprises butylhydroxyltoluene.

25. The soft chewable of any of items 1 to 24 wherein the preservative constitutes at least about 0.01 wt %, at least about 0.05 wt %, at least about 0.1 wt %, or at least about 0.5 wt % of the soft chewable.

26. The soft chewable of any of items 1 to 25 wherein the preservative constitutes from about 0.01 wt % to about 2.0 wt % or from about 0.05 wt % to about 1.0 wt % of the soft chewable.

27. The soft chewable of any of items 1 to 26 wherein the preservative comprises a Paraben.

28. The soft chewable of any of stems 1 to 27 wherein the binder constitutes at least about 0.5 wt %, at least about 1 wt %, at least about 2 wt %, or at least about 3 wt % of the soft chewable.

29. The soft chewable of any of items 1 to 28 wherein the binder constitutes from about 0.3 wt % to about 10 wt %, from about 1 wt % to about 8 wt %, from about 2 wt % to about 6 wt %, or from about 2 wt % to about 5 wt % of the soft chewable.

30. The soft chewable of any of items 1 to 29 wherein the binder comprises polyvinylpyrrolidone.

31. The soft chewable of any of items 1 to 30 wherein water constitutes at least about 2.5 wt %, at least about 5 wt %, or at least about 10 wt % of the soft chewable.

32. The soft chewable of any of items 1 to 31 wherein water constitutes from about 2.5 wt % to about 20 wt %, from about 5 wt % to about 20 wt %, from about 5 wt % to about 15 wt %, from about 10 wt % to about 20 wt % or from about 10 wt % to about 15 wt % of the soft chewable.

33. The soft chewable of any of items 1 to 32 wherein the soft chewable is essentially free of starch.

34. The soft chewable of any of items 1 to 33 wherein the soft chewable is essentially free of oil.

35. The soft chewable of any of items 1 to 34 wherein the soft chewable is essentially free of soya products.

36. The soft chewable of any of items 1 to 35 wherein the soft chewable is essentially free of polyethylene glycol.

37. The soft chewable of any of items 1 to 36 wherein the soft chewable is essentially free of wax.

38. The soft chewable of any of items 1 to 37 wherein the soft chewable further comprises one or more components selected from the group consisting of surfactants or wetting agents, sweeteners, pH stabilizers, and coloring agents.

39. The soft chewable of item 38 wherein the sweetener comprises sodium saccharin.

40. The soft chewable of item 38 or 39 wherein the surfactant comprises sodium laurylsulfate.

41. The soft chewable of any of items 1 to 40 wherein the at least one active ingredient is selected from the group consisting of praziquantel, pyranatel pamoate, febantel, and combinations thereof.

42. The soft chewable of any of items 1 to 41 wherein after storing the soft chewable for about 5 days, about 10 days, about 20 days, about 30 days, about 40 days, or about 60 days, at 40° C., the soft chewable disintegrates in less than about 25 minutes, less than about 20 minutes, or less than about 15 minutes as determined in accordance with method 2.9.1 (Test B) of the European Pharmacopoeia 6.0.

43. A process for preparing a soft chewable, the process comprising:
(a) preparing, at ambient temperature, a mixture comprising at least one active ingredient, a flavoring agent, and a disintegrant;
(b) preparing a granulation fluid comprising a humectant, water, and a binder;
(c) combining under agitation the granulation fluid and the mixture to form a dough;
(d) forming the soft chewable from the dough; and
(e) reducing the moisture content of the soft chewable.

44. The process of item 43 wherein the mixture further comprises an antioxidant.

45. The process of item 43 or 44 wherein the mixture further comprises a preservative.

46. The process of any of items 43 to 45 wherein the granulation fluid further comprises an antioxidant.

47. The process of any of items 43 to 46 wherein the granulation fluid further comprises a preservative.

48. The process of any of items 43 to 47 wherein forming the soft chewable from the dough layer comprises knocking out the soft chewable from the dough layer.

49. The process of any of items 43 to 447 wherein forming the soft chewable from the dough layer comprises molding the soft chewable from the dough layer.

50. The process of any of items 43 to 49 wherein the soft chewable disintegrates in less than about 25 minutes as determined in accordance with method 2.9.1 (Test B) of the European Pharmacopoeia 6.0.

51. The process of any of items 43 to 50 wherein the soft chewable disintegrates in less than about 20 minutes as determined in accordance with method 2.9.1 (Test B) of the European Pharmacopoeia 6.0.

52. The process of any of items 43 to 51 wherein the soft chewable disintegrates in less than about 15 minutes as determined in accordance with method 2.9.1 (Test B) of the European Pharmacopoeia 6.0.

53. The process of any of items 43 to 52 wherein the disintegrant constitutes at least about 10 wt %, at least about 12 wt %, at least about 15 wt %, at least about 17 wt %, at least about 20 wt %, at least about 25 wt %, at least about 30 wt %, at least about 40 wt %, or at least about 50 wt % of the soft chewable.

54. The process of any of items 43 to 53 wherein the disintegrant constitutes from about 10 wt % to about 60 wt %, from about 10 wt % to about 50 wt %, from about 10 wt % to about 40 wt %, from about 10 wt % to about 35 wt %, from about 10 wt % to about 30 wt %, from about 12 wt % to about 30 wt %, or from about 15 wt % to about 30 wt % of the soft chewable.

55. The process of any of items 43 to 54 wherein the disintegrant is selected from the group consisting of carmellose calcium, directly compressible mannitol, crosslinked povidone, croscarmellose sodium, a mixture of directly compressible mannitol and croscarmellose sodium, and combinations thereof.

56. The process of any of items 43 to 55 wherein the disintegrant is selected from the group consisting of a mixture of polyvinyl sodium and directly compressible mannitol, a mixture of croscarmellose sodium and polyvinyl caprolactam-polyvinyl acetate-polyethylene glycol graft copolymer, a mixture of polyvinyl sodium and crosslinked povidone, a mixture of sodium starch glycolate and microcrystalline cellulose, and combinations thereof.

57. The process of any of stems 43 to 58 wherein the disintegrant comprises carmellose calcium.

58. The process of any of items 43 to 57 wherein the disintegrant comprises directly compressible mannitol 59. The process of any of items 43 to 58 wherein the disintegrant comprises a mixture of croscarmellose sodium and directly compressible mannitol.

60. The process of any of items 43 to 59 wherein the disintegrant comprises directly compressible mannitol having a mean particle size of about 200 µm.

61. The process of any of items 43 to 60 wherein the flavoring agent constitutes at least about 1 wt %, at least about 5 wt %, at least about 10 wt %, at least about 15 wt %, at least about 20 wt %, or at least about 25 wt % of the soft chewable.

62. The process of any of items 43 to 61 wherein the flavoring agent constitutes from about 1 wt % to about 40 wt %, from about 5 wt % to about 40 wt %, from about 10 wt % to about 35 wt %, or from about 15 wt % to about 30 wt % of the soft chewable.

63. The process of any of items 43 to 62 wherein the flavoring agent comprises an animal-derived product.

64. The process of any of items 43 to 63 wherein the humectant constitutes at least about 10 wt %, at least about 15 wt %, or at least about 20 wt % of the soft chewable.

65. The process of any of items 43 to 64 wherein the humectant constitutes from about 5 wt % to about 50 wt %, from about 10 wt % to about 45 wt %, from about 15 wt % to about 40 wt %, from about 20 wt % to about 35 wt %, from about 20 wt % to about 30 wt %, or about 25 wt % of the soft chewable.

66. The process of any of items 43 to 65 wherein the humectant comprises glycerin.

67. The process of any of items 43 to 66 wherein the antioxidant constitutes at least about 0.01 wt %, at least about 0.1 wt %, at least about 1 wt %, at least about 2 wt %, or at least about 5 wt % of the soft chewable.

68. The process of any of items 43 to 67 wherein the antioxidant constitutes from about 0.01 wt % to about 15 wt %, from 0.1 wt % to 15 wt %, from about 1 wt % to 10 wt %, 5 wt % to about 15 wt %, or from about 5 wt % to 10 wt % of the soft chewable.

69. The process of any of items 43 to 68 wherein the antioxidant comprises citric acid.

70. The process of any of items 43 to 69 wherein the antioxidant comprises propyl gallate.

71. The process of any of items 43 to 70 wherein the antioxidant comprises butylhydroxyltoluene.

72. The process of any of items 45 to 71 wherein the preservative constitutes at least about 0.01 wt %, at least about 0.05 wt %, at least about 0.1 wt %, or at least about 0.5 wt % of the soft chewable.

73. The process of any of items 45 to 72 wherein the preservative constitutes from about 0.01 wt % to about 2.0 wt % or from about 0.05 wt % to about 1.0 wt % of the soft chewable.

74. The process of any of items 45 to 73 wherein the preservative comprises a paraben.

75. The process of any of items 45 to 74 wherein the binder constitutes at least about 0.5 wt %, at least about 1 wt %, at least about 2 wt %, or at least about 3 wt % of the soft chewable.

76. The process of any of items 43 to 75 wherein the binder constitutes from about 0.5 wt % to about 10 wt %, from about 1 wt % to about 8 wt %, from about 2 wt % to about 6 wt %, or from about 2 wt % to about 5 wt % of the soft chewable.

77. The process of any of items 43 to 76 wherein the binder comprises polyvinylpyrrolidone.

78. The process of any of items 43 to 77 wherein water constitutes at least about 2.5 wt %, at least about 5 wt %, or at least about 10 wt % of the soft chewable.

79. The process of any of items 43 to 78 wherein water constitutes from about 2.5 wt % to about 20 wt %, from about 5 wt % to about 20 wt %, from about 5 wt % to about 15 wt %, from about 10 wt % to about 20 wt % or from about 10 wt % to about 15 wt % of the soft chewable.

80. The process of any of items 43 to 79 wherein the soft chewable is essentially free of starch.

81. The process of any of items 43 to 80 wherein the soft chewable is essentially free of oil.

82. The process of any of items 43 to 81 wherein the soft chewable is essentially free of soya products.

83. The process of any of items 43 to 82 wherein the soft chewable is essentially free of polyethylene glycol.

84. The process of any of items 43 to 83 wherein the soft chewable is essentially free of wax.

85. The process of any of items 43 to 84 wherein the soft chewable further comprises one or more components selected from the group consisting of surfactants or wetting agents, sweeteners, pH stabilizers, and coloring agents.

86. The process of any of items 85 wherein the sweetener comprises sodium saccharin.

87. The process of item 85 or 88 wherein the surfactant comprises sodium laurylsulfate.

88. The process of any of items 43 to 87 wherein the at least one active ingredient is selected from the group consisting of praziquantel pyranatel pamoate, febantel, and combinations thereof.

89. The process of any of items 43 to 88 wherein after storing the soft chewable for about 5 days, about 10 days, about 20 days, about 30 days, about 40 days, or about 60 days, at 40° C., the soft chewable disintegrates in less than about 25 minutes, less than about 20 minutes, or less than about 15 minutes as determined in accordance with method 2.9.1 (Test B) of the European Pharmacopoeia 6.0.

I. Soft Chewable

Active Ingredients

In accordance with the present invention, the soft chewable includes at least one active ingredient. The at least one active ingredient includes any pharmaceutical agent known in the pharmaceutical arts that is suitable for oral administration. The at least one active ingredient may include agents that are, for example, antiparasitic (endo- or ecto-), acaricidic, anthelmintic, insecticidal, antimicrobial, antiviral, antibiotic, anti-inflammatory, psychotropic, proton pump inhibitors, etc.

The active ingredient can be, for example, one or more of the following well-known classes of acaricides including: antibiotic acaricides such as abamectin, doramectin, eprinomectin, ivermectin, milbemectin, nikkomycins, selamectin, tetranectin, and thuringiensin, bridged diphenyl acaricides such as azobenzene, benzoximate, benzyl benzoate, bromopropylate, chlorbenside, chlorfenethol, chlorfenson, chlorfensulphide, chlorbenzilate, chloropropylate, dicofol, diphenyl sulfone, dofenapyn, fenson, fentrifanil, fluorbenside, proclonol, tetradifon, and tetrasul; carbamate acaricides such as benomyl, carbanolate, carbaryl, carbofuran, fenothiocarb, methiocarb, metolcarb, promacyl, and propoxur; oxime carbamate acaricides such as aldicarb, butocarboxim, oxamyl, thiocarboxime, and thiofanox; dinitrophenol acaricides such as binapacryl, dinex, dinobuton, dinocap, dinocap-4, dinocap-6, dinocton, dinopenton, dinosulfon, dinoterbon, and DNOC; formaroidine acaricides such as amitraz, chlordimeform, chloromebuform, formetanate, and formparanate, mite growth regulators such as clofentezine, dofenapyn, fluazuron, flubenzimine, flucycloxuron, flufenoxuron, and hexythiazox; organochlorine acaricides such as bromocyclen, camphechlor, dienochlor, and endosulfan; organotin acaricides such as azocyclotin, cyhexatin, and fenbutatin oxide; pyrazole acaricides such as acetoprole, fipronil and analogues and derivatives thereof, tebufenpyrad, and vaniliprole; pyrethroid acaricides including: pyrethroid ester acaricides like acrinathrin, bifenthrin, cyhalothrin, cypermethrin, alpha-cypermethrin, fenpropathrin, fenvalerate, flucythrinate, flumethrin, fluvalinate, tau-fluvalinate, and permethrin, and pyrethroid ether acaricides like halfenprox; quinoxaline acaricides such as chinomethionat and thioquinox; sulfite ester acaricides such as propargite; tetronic acid acaricides such as spirodiciofen; and form unclassified acaricides such acequinocyl, amidoflumet, arsenous oxide, chloromethiuron, closantel, crotamiton, diafenthiuron, dichiofluanid, disulfiram, fenazaflor, fenazaquin, fenpyroximate, fluacrypyrim, fluenetil, mesulfen, MNAF, nifluridide, pyridaben, pyrimidifen, sulfiram, sulfluramid, sulfur and triarathene.

Suitable insecticides can be selected from a variety of well-known different chemical classes such as chlorinated hydrocarbons, organophosphates, carbamates, pyrethroids, formamidines, borates, phenylpyrazoles, and macrocytic lactones. Prominent insecticides are imidacloprid, fenthion, fipronil, allethrin, resmethrin, fenvalerate, permetrin, malathion and derivatives thereof. According to one embodiment preferred insecticides are those of the neonicotinoid class, for example acetamiprid, clothianidin, dinotefuran, imidacloprid (mentioned above), nitenpyram, thiacloprid and thiamethoxam. Widely used insect growth regulators (IGRs) are, for example benzoylphenylureas such as diflubenzuron, lufenuron, noviflumuron, hexaflumuron, triflumuron, and teflubenzuron or substances like fenoxycarb, pyriproxifen, methoprene, kinoprene, bydroprene, cyromazine, buprofezin, pymetrozine and derivatives thereof.

Suitable anthelmintics can be selected from endo-parasiticides and endecticides including any of the following well-known groups such as macrocyclic lactones, benzimidazoles, pro-benzimidazoles, imidazothiazoies, tetrahydropyrimidines, organophosphates, piperazines, salicylanilide, and cyclic depsipeptides.

Preferred anthelmintics comprise broad spectrum macrocyclic lactones, such as avermectins, milbemycins and derivatives thereof, including ivermectin, doramectin, moxidectin, selamectin, emamectin, eprinomectin, milbemectin, abamectin, milbemycin oxime, nemadectin, and derivatives thereof, in free form or in the form of a pharmaceutical acceptable salt. Benzimidazoles, benzimidazole carbamate and pro-benzimidazoles include potent compounds such as thiabendazole, mebendazole, fenbendazole, oxfendazole, oxibendazole, albendazole, luxabendazole, netobimin, parbendazole, flubendazole, cyclobendazole, febantel, thiophanate and derivatives thereof, imidazothiazoles include highly active compounds such as tetramisole, levamisole, and derivatives thereof. Tetrahydropyrimidines include highly active compounds such as morantel, pyrantel, and derivatives thereof. Organophosphates include potent compounds such as dichlorvos, haloxon, trichlorfon, and derivatives thereof. Salicylanilides include highly active compounds such as closantel, tribromsalan, dibromsalan, oxychlozanide, clioxanide, rafoxanide, brotianide, bromoxanide and derivatives thereof. Cyclic depsipeptides include compounds consisting of amino acids and hydroxycarboxylic acids as ring structural units and 8 to 30 ring atoms, such as PF 1022A, emodepside, and others described in U.S. Pat. No. 6,150,932, which is incorporated herein by reference for all relevant purposes.

Suitable antimicrobial active ingredients are, for example, various penicillins, tetracyclines, sulfonamides, cephalosporins, cephamycins, aminoglucosids, trimethoprim, dimetridazoles, erythromycin, framycetin, fruazolidone, various pleuromutilins such as thiamulin, valnemulin, various macrolides, streptomycin, clopidol, salinomycin, monensin, halofuginone, narasin, robenidine, quinolones, etc. Quinolones, preferably fluoroquinolones, include compounds such as those disclosed in U.S. Pat. Nos. 4,670,444; 4,472,405; 4,730,000; 4,861,779; 4,382,892; and 4,704,459; which are incorporated herein by reference. Specific examples of fluoroquinolones include benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, perfloxacin, temafioxacin, tosufloxacin, sarafloxacin, and sparfloxacin. As an additional example of an antibacterial fluoroquinolone for use in animals pradofloxacin may be mentioned. Specific examples of other quinolones include pipemidic acid and nalidixic acid.

Other pharmaceutical agents known in the veterinary arts, such as vitamins and mineral supplements are also suitable active ingredients.

If feasible, pharmaceutically acceptable salts of any of the active ingredients may be used in the soft chewable. Furthermore, prodrugs of the active ingredients) may also be used in the soft chewable.

In various embodiments, the active ingredient comprises a combination of a macrocyclic lactone and an anthelmintic selected from the group consisting of albendazole, clorsulon, cydectin, diethylcarbamazine, febantel, fenbendazole, haloxon, levamisole, mebendazole, morantel, oxyclozanide, oxibendazole, oxfendazole, oxfendazole, oxamniquine, pyrantel, piperazine, praziquantel, thiabendazole, tetramisole, trichlorfon, thiabendazole, and derivatives thereof.

In various embodiments, the soft chewable comprises an active ingredient selected from the group consisting of praziquantel, pyrantel pamoate, febantel, pharmaceutical acceptable salts thereof, and combinations thereof. In various preferred embodiments, the active ingredient comprises praziquantel, in other embodiments, the active ingredient comprises febantel. In order to broaden the activity spectrum towards ecto-parasites the soft chewable can also contain a combination of anthelmintics, insecticides, and/or aearicides. For example, in various embodiments, the soft chewable comprises praziquantel and pyrantel pamoate, in various other embodiments, the active ingredients comprises praziquantel, pyrantel pamoate, and febantel.

In various embodiments, the active ingredient comprises a depsipeptide selected from the group consisting of PF 1022A, and emodepside. In these and various other embodiments, the active ingredient comprises an ivermectin.

In various embodiments the active ingredient comprises an antimicrobial fluoroquinolone which is preferably selected from the group consisting of enrofloxacin and pradofloxacin.

In accordance with the present invention, the soft chewable contains a pharmaceutically effective amount of at least one active ingredient. As used herein, the term "pharmaceuticafly effective amount" refers to a nontoxic amount of the active ingredient that is capable of producing the desired effect. The amount of active ingredient depends on the active ingredient(s), the animal being treated, the state of condition, and the severity of the conditions. The determination of those factors is well within the level of one skilled in the veterinary arts.

Generally, however, the soft chewable contains about 0.0001 wt % to about 50 wt % of active ingredients) of the soft chewable. In various embodiments, the soft chewable contains active ingredients in amount from about 0.01 wt % to about 40 wt %, from about 0.1 wt % to about 35 wt %, from about 1 wt % to about 30 wt %, from about 5 wt % to about 30 wt %, or from about 10 wt % to about 30 wt %.

The amount of active ingredient in the soft chewable may also be specified, as is typical in the art, in terms of the weight of the active per dosage form (in this case a soft chewable). For example, in various embodiments, the soft chewable contains at least about 5 mg, at least about 10 mg, at least about 20 mg, at least about 30 mg, at least about 40 mg, at least about 50 mg, or at least about 100 mg of active ingredients). In these and other embodiments, the soft chewable contains from about 5 mg to about 2000 mg, from about 10 mg to about 1500 mg, from about 10 mg to about 1000 mg, from about 10 mg to about 500 mg, from about 20 mg to about 2000 mg, from about 20 mg to about 1500 mg, from about 20 mg to about 1000 mg, from about 20 mg to about 500 mg, from about 50 mg to about 2000 mg, from about 50 mg to about 1500 mg, from about 50 mg to about 1000 mg, or from about 50 mg to about 500 mg of active ingredient(s).

The soft chewable may be administered to warm-blooded animals, such as humans, cattle, sheep, pigs, cats, dogs, horses, llamas, deer, rabbits, skunks, raccoons, camels, etc., or birds. In various embodiments, the soft chewable is for administration to dogs, cats, and other companion animals.

Disintegrants

In accordance with the present invention, the soft chewable includes a disintegrant to aid in the break up of the soft chewable upon administration. As used herein, the term "disintegrant" includes conventional disintegrants and other disintegrants known in the art as super-disintegrants. Generally, a soft chewable of the present invention disintegrates in less than about 25 minutes, less than about 20 minutes, or less than about 15 minutes as determined in accordance with method 2.9.1 (Test B) of the European Pharmacopoeia 6.0, which is hereby incorporated herein by reference for all relevant purposes, in various embodiments, soft chewables that have been dried (e.g., moisture content has been reduced to about 10 wt % to about 20 wt %), disintegrate in less than about 25 minutes, less than about 20 minutes, or less than about 15 minutes as determined in accordance with method 2.9.1 (Test B) of the European Pharmacopoeia 6.0. Additionally or alternatively, in various embodiments, the soft chewables disintegrate in less than about 25 minutes, less than about 20 minutes, or less than about 15 minutes after drying and storage at 40° C. and atmospheric pressure in an aluminum foil bags, aluminum blister packs, or similar storage receptacles for at least about 5 days, at least about 10 days, at least about 15 days, at least about 20 days, at least about 25 days, at least about 30 days, at least about 35 days, at least about 40 days, at least about 45 days, or at least about 50 days as determined in accordance with method 2.9.1 (Test B) of the European Pharmacopoeia 6.0.

In various embodiments, the soft chewable comprises at least one disintegrant selected from the group consisting of carmellose calcium (cartooxymethyl cellulose calcium), directly compressible mannitol (e.g., PARTECK M 200, available from Merck; PEARLITOL SD 200, available from Roquette and as described in U.S. Pat. No. 5,573,777, the content of which is hereby incorporated herein by reference), crosslinked povidone (e.g., Kollidon CL, available from BASF), croscarmellose sodium (e.g., AC-DI-SOL, available from FMC), and combinations thereof. Surprisingly, carmellose calcium has been found to be particularly suitable as a disintegrant for the soft chewable of the present invention. Therefore, in various embodiments, the disintegrant comprises carmellose calcium. Directly compressible mannitol has also been found to be particularly suitable as a disintegrant for the soft chewable. Therefore, in various embodiments, the disintegrant comprises directly compressible mannitol. In various preferred embodiments, the directly compressible mannitol has a mean particle size of about 200 μm.

In addition, various mixtures of disintegrants are suitable for the present invention including a mixture of croscarmellose sodium and directly compressible mannitol (e.g., PARTECK ODT, available from Merck), a mixture of croscarmellose sodium (e.g., AC-DI-SOL, available from FMC) and polyvinyl caprolactam-polyvinyl acetate-polyethylene glycol graft copolymer (e.g., SOLUPLUS, available from BASF), a mixture of croscarmellose sodium (e.g., AC-DI-SOL, available from FMC) and crosslinked povidone (e.g., KOLIIDON CL available from BASF), a mixture of sodium starch glycolate (e.g., PRIMOJEL, available from DMV-Fonterra) and micorocrystaillne cellulose (e.g., MICROCEL MC-500) and combinations thereof.

Surprisingly, applicants have discovered that by employing selected disintegrants and in a higher concentration, the disintegrant can effectively provide a substantial portion of the soft chewable matrix which facilitates rapid disintegration of the soft chewable upon administration. Significantly, applicants have found that when a high concentration of disintegrant is employed, the need for additional bodying agents is reduced or even completely eliminated. Accordingly, in various embodiments, the disintegrant(s) constitutes at least about 10 wt %, at least about 12 wt %, at least about 15 wt %, at least about 17 wt %, at least about 20 wt %, at least about 25 wt %, at least about 30 wt %, at least about 40 wt %, or at least about 50 wt % of the soft chewable. In these and various other embodiments, the disintegrant(s) constitutes from about 10 wt % to about 60 wt %, from about 10 wt % to about 50 wt %, from about 10 wt % to about 40 wt %, from about 10 wt % to about 35 wt %, from about 10 wt % to about 30 wt %, from about 12 wt % to about 30 wt %, or from about 15 wt % to about 30 wt % of the soft chewable.

Importantly, in various embodiments of the present invention, the soft chewable is free or essentially free of starches that negatively impact the desired disintegration of the soft chewable and/or dissolution profile of the active ingredient(s), such as corn starch, wheat starch, rice starch, tapioca starch, potato starch, pregelatinized starch, partially gelatinized starch, etc.

Flavoring Agents

In accordance with the present invention, the soft chewable includes a flavoring agent to improve palatability. The flavoring agent may be animal-derived or synthetic. In various embodiments, the flavoring agent is an animal-derived agent, typically having a meat flavor. For example, suitable flavoring agents include chicken liver powder, pork liver powder, beef, ham, fish, or rawhide-derived products. In various embodiments, the soft chewable includes a pork liver powder flavoring agent, in other embodiments, the flavoring agent comprises a synthetic flavoring agent.

Generally, the flavoring agent constitutes at least about 1 wt %, at least about 5 wt %, at least about 10 wt %, at least about 15 wt %, at least about 20 wt %, at least about 25 wt % of the soft chewable. Typically, the flavoring agent constitutes from about 5 wt % to about 40 wt %, more typically from about 10 wt % to about 35 wt %, and still more typically from about 15 wt % to 30 wt % of the soft chewable.

If needed, a flavor enhancing agent such as yeast, yeast extract, or monosodium glutamate may be employed so long as it does not negatively impact the chemical stability of the active ingredient or the desired disintegration characteristics of the soft chewable.

Importantly however, in various embodiments of the present invention, the soft chewable is free or essentially free of soya products. In general, soya products to a certain degree lack uniformity and, as a result, when used as excipients contribute undesirably to inferbatch variations. Thus, a soft chewable that is free or essentially free of soya products beneficially facilitates interbatch uniformity.

Humectants

In accordance with the present invention, the soft chewable includes at least one humectant which serves to soften the soft chewable by maintaining moisture therein. In various embodiments, the humectant comprises glycerin. Other suitable humectants include glycerol triacetate, polydextrose, and lactic acid.

Generally, the humectant constitutes at least about 10 wt %, at least about 15 wt %, or at least about 20 wt % of the soft chewable. Typically, the humectant constitutes from about 5 wt % to about 50 wt %, from about 10 wt % to about 45 wt %, from about 15 wt % to about 40 wt %, from about 20 wt % to about 35 wt %, or from about 20 wt % to about 30 wt % (e.g., about 25 wt %) of the soft chewable.

In various embodiments, the granulation fluid comprises the humectant, and is incorporated into the soft chewable formulation upon combining with the dry ingredients.

Importantly however, in various embodiments of the present invention, the soft chewable formulation is free or essentially free of polyethylene glycol (PEG) and/or propylene glycol. While not being bound by theory, it is currently believed that some bitter-tasting active ingredients (e.g., praziquantel) dissolve in granulation fluid containing PEG or propylene glycol. As a result, the bitter active ingredients are undesirably distributed uniformly throughout the soft chewable and render the soft chewable less palatable.

Moreover, the soft chewable comprises water. Water is typically added as a component of the granulation fluid. Generally, the initial moisture content of the soft chewable before drying is at least about 5 wt %, at least about 10 wt %, or at least about 15 wt % (e.g., 14%±3 wt %). Typically the moisture content of the soft chewable is from about 2.5 wt % to about 25 wt %, from about 5 wt % to about 25 wt %, from about 5 wt % to about 15 wt %, from about 10 wt % to about 20 wt %, or from about 10 wt % to about 15 wt %.

After drying, (e.g., for 20 minutes at 60° C. and atmospheric pressure) the moisture content of the soft chewable is at least about 2.5 wt %, at least about 5 wt %, or at least about 10 wt %. Typically the moisture content of the soft chewable after drying is from about 25 wt % to about 20 wt %, from about 5 wt % to about 20 wt %, from about 5 wt % to about 15 wt %, from about 10 wt % to about 20 wt %, from about 10 wt % to about 15 wt % (e.g., about 13 wt %), or from about 5 wt % to about 15 wt % (e.g. about 10 wt %).

The moisture content of the soft chewable may be determined, for example, by the Karl Fischer Titration method.

Binders

In accordance with the present invention, the soft chewable includes at least one binder, such as polyvinylpyrrolidone, low molecular weight HPMC, alginate, and others well known in the art and described in pharmaceutical texts, in various embodiments, the binder comprises polyvinylpyrrolidone (e.g., Povidone 25).

Typically, the binder constitutes at least about 0.5 wt %, at least about 1 wt %, at least about 2 wt %, or at least about 3 wt % of the soft chewable. In various embodiments, the binder constitutes from about 0.5 wt % to about 10 wt %, from about 1 wt % to about 8 wt %, from about 2 wt % to about 6 wt %, or from about 2 wt % to about 5 wt % of the soft chewable.

In various embodiments, the granulation fluid comprises the binder and, like the humectant, is incorporated into the soft chewable upon combining with the dry ingredients.

Importantly, in various embodiments of the present invention, the soft chewable is free or essentially free of starches that negatively impact the desired disintegration of the soft chewable and/or dissolution profile of the active ingredient(s), such as corn starch, wheat starch, rice starch, tapioca starch, potato starch, pregelatinized starch, partially gelatinized starch, etc.

Antioxidants

In accordance with the present invention the soft chewable also includes at least one antioxidant. Antioxidants increase the shelf-life of the soft chewables (e.g., by limiting degradation and/or oxidation of the flavoring agent). Various antioxidants known in the art are suitable for the present invention. For example, antioxidants include compounds such as BHT (butylated hydroxy toluene), propyl gailate, ascorbic acid, ascrobyl palmitate, fumario acid, malic acid, citric acid, edetic acid and its salts, lecithin, tartaric acid, sodium ascorbate, sodium metabisulfate, BHA (butylated hydroxy anisole), monothioglycerol, Tenox 2, Tenox PG, Tenox s-1, tocopherols (alpha-, beta-, or delta-tocopherol, tocopherol esters, alpha-tocopherol acetate), other alkyl gailates, resveratrol, quercetin, benzoic acid, Trolox (N-acetylcysteine, 6-hydroxy-2,5,7,8-tetramethylchroman-2-carboxylic acid), dimethyl thiourea (DMTU), hesperetin, tetrahydrocurcumin, tetrahydrodemethoxycurcumin, and the like. Generally, the antioxidant constitutes at least about 0.01 wt %, at least about 0.1 wt %, at least about 1 wt %, at least about 2 wt %, or at least about 5 wt % of the soft chewable. In various embodiments, the antioxidant constitutes from about 0.01 wt % to about 15 wt %, from 0.1 wt % to 15 wt %, from about 1 wt % to 10 wt %, 5 wt % to about 15 wt %, or from about 5 wt % to 10 wt % of the soft chewable.

In various embodiments, the antioxidant includes propyl gallate and/or citric acid. In these and various other embodiments, the antioxidant includes BHT.

In various embodiments, the granulation fluid comprises the antioxidant and is incorporated into the soft chewable formulation upon combining with the dry ingredients. Including the antioxidant in the granulation fluid facilitates homogeneous distribution of the antioxidant throughout the chewable.

Preservatives

In accordance with a preferred embodiment of the present invention the soft chewable also includes at least one preservative. Preservatives also increase the shelf-life of the soft chewables (e.g., by limiting fungal growth). Various preservatives known in the art are suitable for the present invention. Preservatives include, for example, benzalkonium chloride, benzethonium chloride, benzoic acid, benzyl alcohol, bronopol, parabens (e.g., methylparaben, ethylparaben, propylparaben, butylparaben), cetrimide, chlorhexidine, chlorobutanol, chlorocresol, cresol, imidurea, phenol, phenoxyethanol, phenylethyl alcohol, phenylmercuric acetate, phenylmercuric borate, phenylmercuric nitrate, potassium sorbate, sodium benzoate, sodium propionate, sorbic acid, thiroerosal, myristyl gama-picolinium chloride, quaternary ammonium compounds, and the like. The preservative(s) generally constitutes at least about 0.01 wt %, at least about 0.05 wt %, at least about 0.1 wt %, or at least about 0.5 wt % of the soft chewable. In various embodiments, the preservative (s) constitute from about 0.01 wt % to about 2.0 wt % or from about 0.05 wt % to about 1.0 wt % of the soft chewable.

In various embodiments, the preservative comprises a paraben.

In various embodiments, the granulation fluid comprises the preservative and is incorporated into the soft chewable formulation upon combining with the dry ingredients, including the preservative in the granulation fluid facilitates homogeneous distribution of the preservative throughout the chewable.

Other Ingredients

Additionally, the soft chewable may contain other ingredients known in the art such as surfactants/wetting agents, pH stablllizers, sweeteners, and coloring agents.

Surfactants or wetting agents may be added the soft chewable to facilitate solubilization of the active ingredient, to prevent crystallization, and to prevent phase separation. Suitable surfactants include, for example, sodium laurylsulfate, sorbitan esters, polyvinyl alcohol, polysorbate 80, poloxamers (e.g., Poloxamer 124, 188, 338, and 407), etc. in various embodiments, the soft chewable comprises sodium laurylsulfate. Also Vitamin E TPGS (D-alpha tocopherol polyethylene glycol 1000 succinate) has emulsifying and solubilizing properties in addition to other properties (absorption enhancer, source of vitamin E) and may be added to the present soft chewable.

In various embodiments, the granulation fluid comprises the surfactant (e.g., sodium laurylsulfate), and is incorporated into the soft chewable formulation upon combining with the dry ingredients.

Importantly however, in various embodiments of the present invention, the soft chewable formulation is free or essentially free of oils such as castor oil, mineral oil, vegetable oils such as corn oil, peanut oil, olive oil, or soybean oil, etc. Moreover, in these and various other embodiments, the soft chewable formulation is free or essentially free of waxes.

The soft chewable may also include pH stabilizers. Such compounds are well known in the art and include, for example, acetic acid/acetate, malic acid/malate, citric acid/citrate, tataric acid/tartrate, lactic acid/lactate, phosphoric acid/phosphate, glycine/glycimate, tris, glutamic acid/glutamates and sodium carbonate.

The soft chewable may include various coloring agents. Coloring agents are known in the art and include, for example, organic dyes, lake pigments, natural colorants such as caramel, and mineral pigments based upon, for example, iron oxide or titanium dioxide.

The soft chewable may also include various sweeteners such as sodium saccharin, xylitol, maltitol, aspartame, sodium cyclamate, and sucralose. In various embodiments, the soft chewable comprises sodium saccharin.

In various embodiments, the granulation fluid comprises the sweetener (e.g., sodium saccharin), and is incorporated into the soft chewable formulation upon combining with the dry ingredients.

In particular embodiments, the soft chewable comprises sodium laurylsulfate, and sodium saccharin. In other embodiments, the soft chewable comprises propyl gallate, citric acid, sodium laurylsulfate, and sodium saccharin.

II. Preparation Process

The present invention is also directed to a process for preparing the improved soft chewable described above.

In accordance with the present invention, the process includes preparing a mixture comprising dry components. In other embodiments, the dry components include at least one active ingredient, a disintegrant, and a flavoring agent. In these and various other embodiments, the dry components include at least one active ingredient, a disintegrant, a flavoring agent, an antioxidant, and a preservative. Preparing the mixture includes mixing dry components in a mixer at room temperature (i.e., from about 20 C. to 25° C.) without applying heat until a homogeneous mixture is achieved.

The process also includes preparing a granulation fluid. In various embodiments, the granulation fluid comprises water, a humectant, and a binder, in these and various other embodiments, the granulation fluid comprises water, a humectant, a binder, an antioxidant, and a preservative. Additionally, the granulation fluid may further comprise a surfactant or wetting agent, a sweetener, and/or coloring agent.

Following preparation of the mixture comprising the dry components and the granulation fluid, the mixture and fluid are combined in a mixer (e.g., a low-shear planetary mixer) in relative proportions sufficient to produce a moist homogeneous dough having the desired initial moisture content.

The homogeneous dough is then formed into soft chewables. Acceptable methods of forming the soft chewables from the dough include methods known in the art and food industry. In punch-out or knock-out methods, the dough is spread as a thin layer. Typically, the dough layer has a thickness from about 2 mm to about 10 mm, from about 2 mm to about 8 mm, from about 2 mm to about 8 mm, or from about 25 mm to about 5 mm. The dough layer may be formed using apparatus well known in the art and in the food industry, such as dough rollers, presses, spreaders, etc. Once the dough layer is formed, soft chewables are punched out from the dough layer (e.g., having a diameter of about 20-30 mm if a circular die is used). Other acceptable methods of forming the soft chewables from the dough include, for example, molding techniques (e.g., by means of a molding machine such as model FORMAX F6 available from the Formax Corporation), in certain embodiments, however, the method for forming the soft chewables does not include extrusion. Regardless of the method of forming, the soft chewable may take the form of any shape (e.g., circular, fish, bone, etc.).

Following formation, the soft chewables are dried until the moisture content is reduced (e.g., reduced to about 12 wt % (±5%) or to e.g. about 10 wt % (±5%). After drying, the soft chewables may be packaged for storage (e.g., in aluminum foil bags, aluminum blister packs, etc.).

The following examples are simply intended to further illustrate and explain the present invention. The examples, therefore, should not be regarded as limiting the scope of the invention or manner in which it may be practiced.

Example 1

In this example, soft chewable treats comprising various active ingredients and disintegrants were prepared and disintegration times were measured in accordance with the standardized test protocol.

Active ingredients (1) praziquantel (2)pyrantel embonate, and (3) febantel (microfine) were mixed homogeneously with pork liver powder, a disfinfegrant, any preservatives, and any antioxidants in the proportions shown on Tables 1-3 in a mixer at room temperature (20° C. to 25° C.) without applying any heat. Granulation fluid consisting of glycerin, purified water. Povidone 25, sodium saccharin, sodium laurylsulfate in the proportions shown on Tables 1-3 was added slowly to the mixer (e.g., a low-shear planetary mixer, available from Kenwood) and mixed for a short time (approximately 1-2 min) until a wet homogeneous dough was formed. The dough was then spread as a sheet by passing through a lab scale machine (e.g., a Haussler L30 dough spreading machine).

Soft chewable treats of the diameter indicated in Tables 1-3 were punched out from the dough layer and dried at approximately SOX until the moisture content was reduced to 12±5 wt % (i.e., for about 20 minutes). The moisture content of each dried treat was determined by the Karl Fischer Titration method (K.F.).

Figure 2:
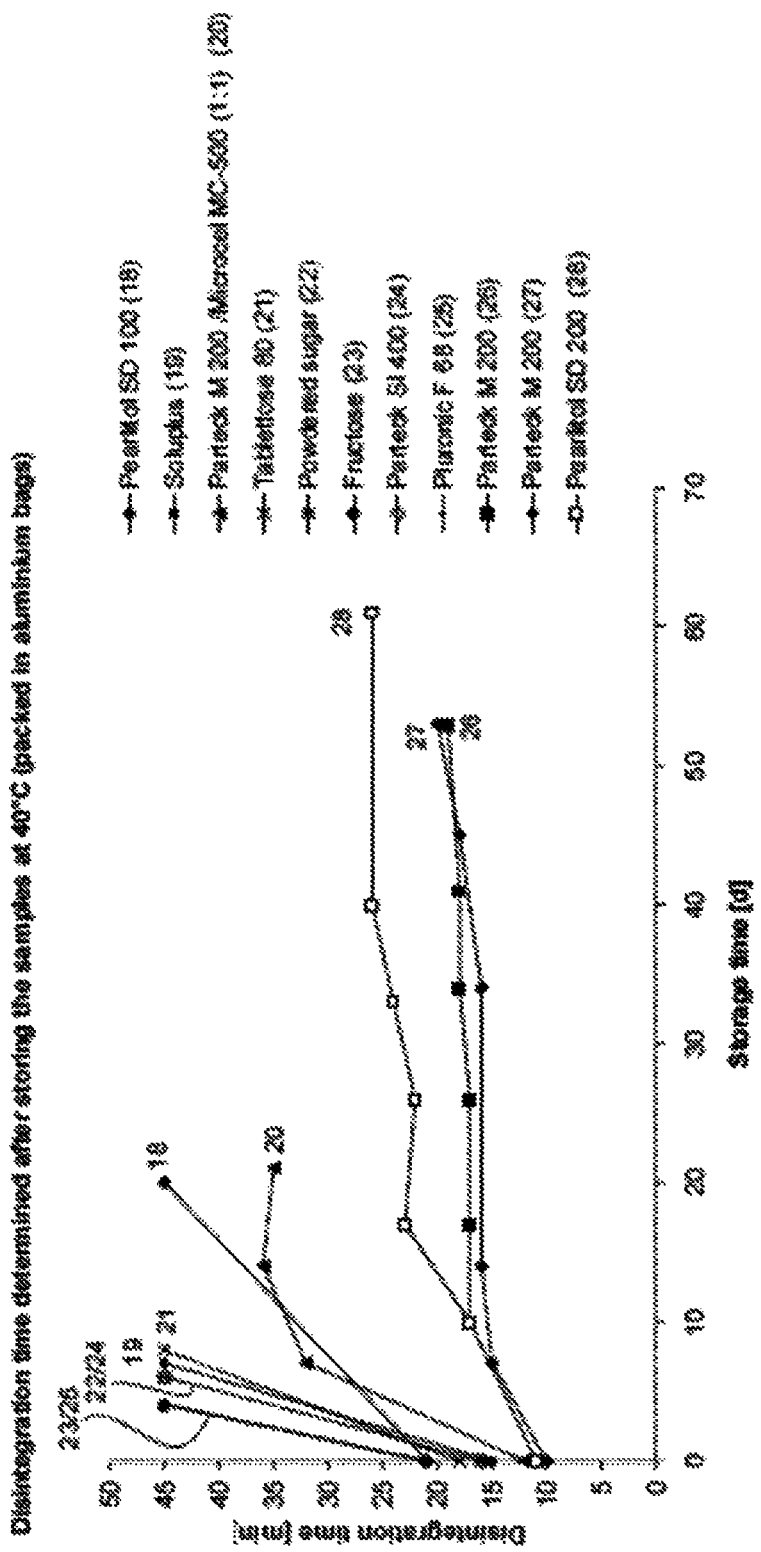
FIG. 2 shows a plot of the disintegration time for soft chewable treats containing various disintegrants as described in Example 1.
Figure 3:
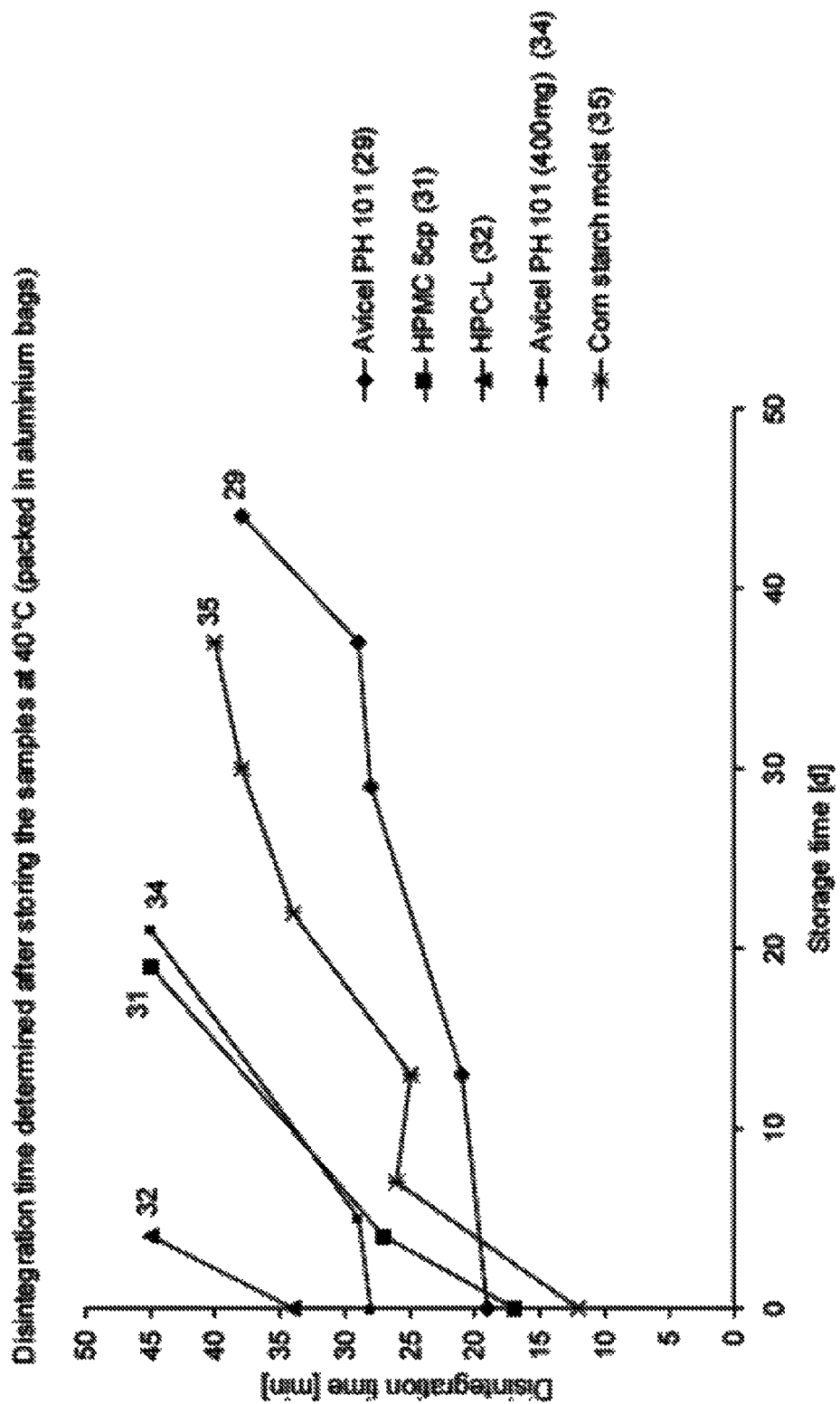
FIG. 3 shows a plot of the disintegration time for soft chewable treats containing various disintegrants as described in Example 1.

Treats were subjected to disintegration method 2.9.1 (Test B) of the European Pharmacopoeia 6.0, at various stages after formation of the treats. Tables 1-3 show results of the disintegration tests for the treats that were tested before the treats were dried. FIGS. 1-3 show the results of the disintegration tests for the treats after drying at 60° C. for about 20 minutes and before or after several days of storage in aluminum foil bags at 40° C., Disintegration results for treat formulations 3, 4, 11, 30, and 33 are not provided in FIGS. 1-3, Disintegration times for these treat formulations exceeded 45 minutes.

Notably, among the disintegrants tested, carmellose calcium was found to be the best disintegrant since the disintegration time remained practically unchanged even upon storage at 40° C. in an aluminum foil bag. The disintegration times for the soft chewable treats made with PARTECK M 200 and PARTECK ODT were also found to be fairly constant on storage.

TABLE 1

| Ingredients | | Soft Chewable Formulation | | | | | | | | |
|---|---|---|---|---|---|---|---|---|---|---|
| | | 1 | 2 | 3 | 4 | 5 | 6 | 7 | 8 | 9 |
| Praziquantel | mg/treat | 50 | 50 | 50 | 50 | 50 | 50 | 50 | 50 | 50 |
| Pyrantel embonate | mg/treat | 144 | 144 | 144 | 144 | 144 | 144 | 144 | 144 | 144 |
| Febantel microfine | mg/treat | 150 | 150 | 150 | 150 | 150 | 150 | 150 | 150 | 150 |
| Pork liver powder | mg/treat | 380 | 380 | 360 | 380 | 380 | 380 | 380 | 380 | 380 |
| Citric Acid | mg/treat | — | — | — | — | — | — | — | — | — |
| Propyl gallate | mg/treat | — | — | — | — | — | — | — | — | — |
| Kollidon CL (Croslinked povidone) | mg/treat | 100 | — | — | — | — | 400 | 800 | — | — |
| Kollidon 12 PF (Povidone) | mg/treat | — | — | — | — | — | — | — | — | — |
| Polyplasdone XL 10 (Croslinked povidone) | mg/treat | — | — | — | — | — | — | — | — | — |
| Ac-Di-Sol (Croscarmellose sodium) | mg/treat | 100 | 200 | — | — | — | — | — | 400 | 800 |
| Primogel (Sodium starch glycollate) | mg/treat | — | — | — | — | — | — | — | — | — |
| Carmellose Calcium (Calcium carboxymethylcellulose) | mg/treat | — | — | — | — | — | — | — | — | — |
| Ludiflash (coprocessed d-mannitol, crospovidone, polyvinyl acetate and povidone) | mg/treat | — | — | — | — | — | — | — | — | — |
| Parteck ODT (Combination of spray dried mannitol (BET>2 $m^2/g$) & croscarmellose sodium) | mg/treat | — | — | — | 200 | 200 | — | — | — | — |
| Pearlitol Flash (Directly compressible mannitol and starch, 80:20) | mg/treat | — | — | 200 | — | — | — | — | — | — |
| Soluplus (Polyvinyl caprolactam-polyvinyl acetate - polyethylene glycol graft copolymer) | mg/treat | — | — | — | — | — | — | — | — | — |
| Microcel MC-500 (Microcrystalline cellulose) | mg/treat | — | — | — | — | — | — | — | — | — |
| Glycerin | mg/treat | 547.8 | 730.4 | 335.5 | 366.6 | 366.6 | 825.8 | 1341.9 | 1101.0 | 1654.0 |
| Povidone 25 | mg/treat | 102.5 | 102.5 | 47.1 | 51.4 | 51.4 | 115.8 | 188.3 | 154.5 | 232.1 |
| Sodium saccharin | mg/treat | 4.2 | 4.2 | 1.9 | 2.1 | 2.1 | 4.8 | 7.7 | 6.3 | 9.5 |
| Sodium laurylsulfate | mg/treat | 3.0 | 3.0 | 1.4 | 1.5 | 1.5 | 3.4 | 5.5 | 4.5 | 6.8 |
| Purified water | mg/treat | 547.8 | 365.2 | 167.7 | 183.3 | 183.3 | 412.9 | 670.9 | 550.5 | 827.0 |
| Total weight, mg | | 2129.4 | 2129.4 | 1477.6 | 1528.9 | 1528.9 | 2486.7 | 3738.3 | 2940.9 | 4253.4 |
| Diameter, mm | | 25 | 26 | 20 | 20 | 26 | 26 | 26 | 26 | 26 |
| Thickness, mm | | NA | 4.4 | 4.0 | 4.2 | 3.1 | 5.2 | 8.0 | 5.8 | 8.2 |
| Moisture after drying (K.F.), % | | NA | 14 | NA | 11 | 12 | 14 | NA | 17 | 17 |
| Disintegration Time before drying, 3 treats (min/min/min) | | 08/08/09 | 09/09/10 | 17/17/18 | 14/14/14 | 08/09/09 | 14/15/15 | 18/20/22 | 10/10/10 | 12/12/12 |

TABLE 1-continued

| Ingredients | | Soft Chewable Formulation | | | | | | | | |
|---|---|---|---|---|---|---|---|---|---|---|
| | | 10 | 11 | 12A | 12B | 13 | 14 | 15 | 16 | 17 |
| Praziquantel | mg/treat | 50 | 50 | 50 | 50 | 50 | 50 | 50 | 50 | 50 |
| Pyrantel embonate | mg/treat | 144 | 144 | 144 | 444 | 144 | 144 | 144 | 144 | 144 |
| Febantel microfine | mg/treat | 150 | 150 | 150 | 150 | 150 | 150 | 150 | 150 | 150 |
| Pork liver powder | mg/treat | 380 | 380 | 380 | 380 | 380 | 380 | 380 | 380 | 380 |
| Citric Acid | mg/treat | — | — | — | — | — | — | 100 | — | — |
| Propyl gallate | mg/treat | — | — | — | — | — | — | 50 | — | — |
| Kollidon CL (Croslinked povidone) | mg/treat | — | — | — | — | — | — | — | — | — |
| Kollidon 12 PF (Povidone) | mg/treat | — | 100 | — | — | — | — | — | — | — |
| Polyplasdone XL 10 (Croslinked povidone) | mg/treat | — | — | — | — | — | — | — | 200 | — |
| Ac-Di-Sol (Croscarmellose sodium) | mg/treat | 100 | — | — | — | — | 160 | — | — | — |
| Primogel (Sodium starch glycolate) | mg/treat | — | — | — | — | 100 | — | 200 | — | — |
| Carmellose Calcium (Calcium carboxymethylcellulose) | mg/treat | — | — | 200 | 200 | — | — | — | — | — |
| Ludiflash (coprocessed d-mannitol, crospovidone, polyvinyl acetate and povidone) | mg/treat | — | — | — | — | — | — | — | — | 200 |
| Parteck ODT (Combination of spray dried mannitol (BET>2 m²/g) & croscarmellose sodium) | mg/treat | — | — | — | — | — | — | — | — | — |
| Pearlitol Flash (Directly compressible mannitol and starch, 80:20) | mg/treat | — | — | — | — | — | — | — | — | — |
| Soluplus (Polyvinyl caprolactam-polyvinyl acetate - polyethylene glycol graft copolymer) | mg/treat | 100 | — | — | — | — | 40 | — | — | — |
| Microcel MC-500 (Microcrystalline cellulose) | mg/treat | — | 100 | — | — | 100 | — | — | — | — |
| Glycerin | mg/treat | 593.6 | 276.3 | 438.7 | 438.7 | 387.1 | 645.2 | 331.5 | 567.8 | 361.3 |
| Povidone 25 | mg/treat | 83.3 | 38.8 | 61.6 | 61.6 | 54.3 | 90.5 | 46.5 | 79.7 | 50.7 |
| Sodium saccharin | mg/treat | 3.4 | 1.6 | 2.5 | 2.5 | 2.2 | 3.7 | 1.9 | 3.3 | 2.1 |
| Sodium laurylsulfate | mg/treat | 2.4 | 1.1 | 1.8 | 1.8 | 1.6 | 2.7 | 1.4 | 2.3 | 1.5 |
| Purified water | mg/treat | 296.8 | 138.1 | 219.4 | 219.4 | 193.6 | 322.6 | 165.8 | 283.9 | 180.7 |
| Total weight, mg | | 1903.5 | 1379.9 | 1648.0 | 1648.0 | 1562.8 | 1988.7 | 1621.1 | 1860.9 | 1520.2 |
| Diameter, mm | | 26 | 26 | 26 | 26 | 26 | 26 | 26 | 26 | 26 |
| Thickness, mm | | 3.7 | 2.5 | 3.2 | 3.2 | 3.2 | 3.9 | 3.0 | 3.4 | 2.8 |
| Moisture after drying (K.F.), % | | 13 | 9 | 11 | NA | 10 | 15 | 10 | 13 | 10 |
| Disintegration Time before drying, 3 treats (min/min/min) | | 10/10/10 | 13/13/13 | 06/06/07 | NA | 06/06/07 | 08/08/08 | 06/07/07 | 11/11/11 | 09/09/10 |

NA: Not measured.

TABLE 2

| Ingredient | | Soft Chewable Formulation | | | | | | | | | | |
|---|---|---|---|---|---|---|---|---|---|---|---|---|
| | | 18 | 19 | 20 | 21 | 22 | 23 | 24 | 25 | 26 | 27 | 28 |
| Praziquantel | mg/treat | 50 | 50 | 50 | 50 | 50 | 50 | 50 | 50 | 50 | 50 | 50 |
| Pyrantel embonate | mg/treat | 144 | 144 | 144 | 144 | 144 | 144 | 144 | 144 | 144 | 144 | 144 |
| Febantel microfine | mg/treat | 150 | 150 | 150 | 150 | 150 | 150 | 150 | 150 | 150 | 150 | 150 |
| Pork liver powder | mg/treat | 380 | 380 | 380 | 380 | 380 | 380 | 380 | 380 | 380 | 380 | 380 |
| Citric Acid | mg/treat | — | — | — | 100 | 100 | 100 | 100 | 100 | — | — | — |
| Propyl galiate | mg/treat | — | — | — | 50 | 50 | 50 | 50 | 50 | — | — | — |
| Fructose | mg/treat | — | — | — | — | — | 200 | — | — | — | — | — |
| Powdered Sugar | mg/treat | — | — | — | — | 200 | — | — | — | — | — | — |
| Tablettose 80 (Lactose monohydrate) | mg/treat | — | — | — | 200 | — | — | — | — | — | — | — |
| Parteck M 200 (Spray dried mannitol for direct compression - mean particle size in μm ->200) | mg/treat | — | — | 100 | — | — | — | — | — | 200 | 200 | — |

TABLE 2-continued

| | | Soft Chewable Formulation | | | | | | | | | | |
|---|---|---|---|---|---|---|---|---|---|---|---|
| Ingredient | | 18 | 19 | 20 | 21 | 22 | 23 | 24 | 25 | 26 | 27 | 28 |
| Parteck SI 400 (Spray dried sorbitol for direct compression - mean particle size >400 μm) | mg/treat | — | — | — | — | — | — | 200 | — | — | — | — |
| Pearlitol SD 100 (Spray dried mannitol - mean particle size 100 μm) | mg/treat | 200 | — | — | — | — | — | — | — | — | — | — |
| Pearlitol SD 200 (Spray dried mannitol - mean particle size 200 μm) | mg/treat | — | — | — | — | — | — | — | — | — | — | 200 |
| Pluronic F 68 (Blockcopolymer surfactant) | mg/treat | — | — | — | — | — | — | — | 200 | — | — | — |
| Soluplus (Polyvinyl caprolactam-polyvinyl acetate - polyethylene glycol graft copolymer) | mg/treat | — | 200 | — | — | — | — | — | — | — | — | — |
| Microcel MC-500 (microcrystalline cellulose) | mg/treat | — | — | 100 | — | — | — | — | — | — | — | — |
| Glycerin | mg/treat | 361.3 | 322.6 | 335.5 | 303.9 | 276.3 | 276.3 | 276.3 | 276.3 | 335.5 | 335.5 | 335.5 |
| Povidone 25 | mg/treat | 50.7 | 45.3 | 47.1 | 42.6 | 38.8 | 38.8 | 38.8 | 38.8 | 47.1 | 47.1 | 47.1 |
| Sodium saccharin | mg/treat | 2.1 | 1.9 | 1.9 | 1.8 | 1.6 | 1.6 | 1.6 | 1.6 | 1.9 | 1.9 | 1.9 |
| Sodium laurylsulfate | mg/treat | 1.5 | 1.3 | 1.4 | 1.3 | 1.1 | 1.1 | 1.1 | 1.1 | 1.4 | 1.4 | 1.4 |
| Purified water | mg/treat | 180.6 | 161.3 | 167.7 | 151.9 | 138.1 | 138.1 | 138.1 | 138.1 | 167.7 | 167.7 | 167.7 |
| Total weight, mg | | 1520.1 | 1456.3 | 1477.6 | 1575.4 | 1529.9 | 1529.9 | 1529.9 | 1529.9 | 1477.6 | 1477.6 | 1477.6 |
| Diameter, mm | | 20 | 26 | 26 | 26 | 26 | 26 | 26 | 26 | 26 | 26 | 26 |
| Thickness, mm | | 4.5 | 2.9 | 2.6 | 2.9 | 2.8 | 2.70 | 2.8 | 2.8 | 2.7 | 2.7 | 2.7 |
| Moisture after drying, (K.F.), % | | NA | 9 | 10 | 10 | 11 | 11 | 10 | 10 | 10 | NA | 10 |
| Disintegration Time before drying, 3 treats (min/min/min) | | 15/15/16 | 10/10/10 | 10/10/11 | 11/11/12 | 09/09/09 | 11/12/12 | 09/10/10 | 18/19/19 | 10/10/11 | N/A | 09/09/09 |

NA: Not measured.

TABLE 3

| | | Soft Chewable Formulation | | | | | | |
|---|---|---|---|---|---|---|---|---|
| Ingredient | | 29 | 30 | 31 | 32 | 33 | 34 | 35 |
| Praziquantel | mg/treat | 50 | 50 | 50 | 50 | 50 | 50 | 50 |
| Pyrantel embonate | mg/treat | 144 | 144 | 144 | 144 | 144 | 144 | 144 |
| Febantel microfine | mg/treat | 150 | 150 | 150 | 150 | 150 | 150 | 150 |
| Pork liver powder | mg/treat | 380 | 380 | 380 | 380 | 380 | 380 | 380 |
| Citric Acid | mg/treat | — | — | 100 | 100 | 100 | — | — |
| Propyl gallate | mg/treat | — | — | 50 | 50 | 50 | — | — |
| HPMC 5 cp (Hydroxypropyl-cellulose of 5 cp viscosity (2% solution at 25° C.)) | mg/treat | — | — | 200 | — | — | — | — |
| HPC-L (Hydroxypropylcellulose of low viscosity) | mg/treat | — | — | — | 200 | — | — | — |
| Avicel PH 101 (Miorocrystalline cellulose) | mg/treat | 200 | — | — | — | — | 400 | — |
| Microcel MC-500 (micro-crystalline cellulose) | mg/treat | — | — | — | — | — | — | — |
| Corn Starch (Wet) | mg/treat | — | — | — | — | — | — | 200 |
| Emcompress Anhydrous (Calcium hydrogen phosphate) | mg/treat | — | — | — | — | 200 | — | — |
| Vitamin E TPGS | mg/treat | — | 200 | — | — | — | — | — |
| Glycerin | mg/treat | 541.9 | 206.5 | 386.8 | 331.5 | 331.5 | 592.8 | 387.1 |
| Povidone 25 | mg/treat | 76.0 | 29.0 | 54.3 | 46.5 | 46.5 | 83.2 | 54.3 |

TABLE 3-continued

| Ingredient | | Soft Chewable Formulation | | | | | | |
|---|---|---|---|---|---|---|---|---|
| | | 29 | 30 | 31 | 32 | 33 | 34 | 35 |
| Sodium saccharin | mg/treat | 3.1 | 1.2 | 2.2 | 1.9 | 1.9 | 3.4 | 2.2 |
| Sodium laurylsulfate | mg/treat | 2.2 | 0.9 | 1.6 | 1.4 | 1.4 | 2.4 | 1.6 |
| Purified water | mg/treat | 270.9 | 103.2 | 193.4 | 165.8 | 165.8 | 296.4 | 193.6 |
| Total weight, mg | | 1818.2 | 1264.7 | 1712.2 | 1621.1 | 1621.1 | 2102.3 | 1562.8 |
| Diameter, mm | | 26 | 26 | 26 | 26 | 26 | 26 | 26 |
| Thickness, mm | | 4.0 | NA | 3.2 | 2.9 | 2.9 | 4.0 | NA |
| Moisture after drying (K.F.), % | | 13 | NA | 10 | 10 | 10 | 14 | 11 |
| Disintegration Time before drying, 3 treats (min/min/min) | | 17/17/18 | 22/22/22 | 16/16/16 | 12/12/13 | 13/13/14 | 26/26/26 | 10/10/11 |

NA: Not measured.

TABLE 4

| Ingredient | | Soft Chewable Formulation | |
|---|---|---|---|
| | | 36 | 37 |
| Enrofloxacin | mg/treat | 50 | — |
| Pradofloxacin | mg/treat | — | 50 |
| Pork liver powder | mg/treat | 380 | 380 |
| Propyl gallate | mg/treat | 3.26 | 3.26 |
| Methyl paraben | mg/treat | 1.46 | 1.46 |
| Propyl paraben | mg/treat | 0.16 | 0.16 |
| Parteck ODT (Combination of spray dried mannitol (BET > 2 m²/g) & croscarmellose sodium) | mg/treat | 494 | 494 |
| Glycerin | mg/treat | 389.65 | 389.65 |
| Povidone 25 | mg/treat | 54.68 | 54.68 |
| Sodium saccharin | mg/treat | 2.24 | 2.24 |
| Sodium laurylsulfate | mg/treat | 1.61 | 1.61 |
| Purified water | mg/treat | 194.83 | 194.83 |
| Total weight, mg | | 1571.9 | 1571.9 |
| Diameter, mm | | 26 | 26 |
| Thickness, mm | | 2.3 | 2.3 |
| Moisture after drying, (K.F.), % | | 11 | 11 |
| Disintegration Time (min) | | 9 | 9 |

In view of the above, it will be seen that the several objects of the invention are achieved and other advantageous results attained.

As various changes could be made in the above formulations, products, and processes without departing from the scope of the invention, it is intended that all matter contained in the above description and shown in the accompanying figures shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A chewable veterinary formulation comprising:
   (a) a pharmaceutically effective amount of at least one antiparasitic active ingredient;
   (b) an animal-derived flavoring agent;
   (c) a disintegrant selected from the group consisting of carmellose calcium,
      directly compressible mannitol, and
      a mixture or combination of croscarmellose sodium and directly compressible mannitol;
   (d) a humectant;
   (e) a binder;
   (f) an antioxidant;
   (g) optionally a preservative; and
   (h) at least 5 wt % water;
   wherein
      the disintegrant constitutes at least about 10 wt % of the chewable veterinary formulation;
      the humectant constitutes at least about 10 wt % of the chewable veterinary formulation;
      the chewable veterinary formulation is essentially free of polyethylene glycol (PEG), propylene glycol, starch, soya products, and wax;
      the chewable veterinary formulation has a disintegration time of less than about 25 minutes, as determined in accordance with method 2.9.1 (Test B) of the European Pharmacopoeia 6.0, measured on treats of the test chewable having a thickness of ≤3.2 mm and a diameter of 26 mm; and
      the disintegration time remains on a nearly constant level after storing the soft chewable veterinary formulation for at least about 35 days at 40° C. and atmospheric pressure.

2. The chewable veterinary formulation of claim 1 comprising (g) a preservative.

3. The chewable veterinary formulation of claim 1, wherein the nearly constant disintegration time of the chewable veterinary formulation is less than about 20 minutes as determined in accordance with method 2.9.1 (Test B) of the European Pharmacopoeia 6.0 measured on treats of the test chewable having a thickness of ≤3.2 mm and a diameter of 26 mm.

4. The chewable veterinary formulation of claim 1 wherein the disintegrant constitutes at least about 12 wt %, at least about 15 wt %, at least about 17 wt %, at least about 20 wt %, at least about 25 wt %, at least about 30 wt %, at least about 40 wt %, or at least about 50 wt % of the chewable veterinary formulation.

5. The chewable veterinary formulation of claim 1 wherein the flavoring agent constitutes at least about 5 wt %, at least about 10 wt %, at least about 15 wt %, at least about 20 wt %, or at least about 25 wt % of the chewable veterinary formulation.

6. The chewable veterinary formulation of claim 1 wherein the humectant constitutes at least about 15 wt %, or at least about 20 wt % of the chewable veterinary formulation.

7. The chewable veterinary formulation of claim 1 wherein the antioxidant constitutes at least about 0.01 wt %, at least about 0.1 wt %, at least about 1 wt %, at least about 2 wt %, or at least about 5 wt % of the chewable veterinary formulation.

8. The chewable veterinary formulation of claim 1 wherein the binder constitutes at least about 0.5 wt %, at least about 1 wt %, at least about 2 wt %, or at least about 3 wt % of the chewable veterinary formulation.

9. The chewable veterinary formulation of claim 1, wherein the water constitutes at least about 10 wt % of the chewable veterinary formulation.

10. The chewable veterinary formulation of claim 1 wherein the chewable veterinary formulation further comprises one or more components selected from the group consisting of surfactants or wetting agents, sweeteners, pH stabilizers, and coloring agents.

11. The chewable veterinary formulation of claim 1 wherein the at least one antiparasitic active ingredient is selected from the group consisting of praziquantel, pyranatel pamoate, febantel, and combinations thereof.

12. A process for preparing the chewable veterinary formulation of claim 1, the process comprising:

(a) preparing, at ambient temperature, a mixture comprising at least one antiparasitic active ingredient, an animal-derived flavoring agent, and a disintegrant, wherein the disintegrant is selected from the group consisting of:
carmellose calcium,
directly compressible mannitol, and
a mixture or combination of croscarmellose sodium and directly compressible mannitol;
(b) preparing a granulation fluid comprising a humectant, antioxidant, water, and a binder;
(c) combining under agitation the granulation fluid and the mixture to form a dough;
(d) forming the chewable veterinary formulation from the dough; and
(e) reducing the moisture content of the chewable veterinary formulation to an amount of at least 5 wt %.

13. The chewable veterinary formulation of claim 1, wherein the animal-derived flavoring agent is selected from the group consisting of chicken liver powder, pork liver powder, beef, ham, fish, and a rawhide-derived product.

\* \* \* \* \*